US006551299B2

(12) United States Patent
Miyoshi et al.

(10) Patent No.: US 6,551,299 B2
(45) Date of Patent: Apr. 22, 2003

(54) ADAPTER FOR MIXING AND INJECTION OF PREPARATIONS

(75) Inventors: Jun Miyoshi, Osaka (JP); Takashi Nakagawa, Osaka (JP)

(73) Assignee: Nipro Corp., Osaka (JP)

( * ) Notice: Subject to any disclaimer, the term of this patent is extended or adjusted under 35 U.S.C. 154(b) by 0 days.

(21) Appl. No.: 09/828,923

(22) Filed: Apr. 10, 2001

(65) Prior Publication Data

US 2001/0029360 A1 Oct. 11, 2001

(30) Foreign Application Priority Data

Apr. 10, 2000 (JP) ....................................... 2000-107697

(51) Int. Cl.[7] ................................................ A61B 19/00
(52) U.S. Cl. ........................ 604/403; 604/411; 604/413
(58) Field of Search ................................ 604/140, 141, 604/148, 403, 411, 412, 413, 414, 905

(56) References Cited

U.S. PATENT DOCUMENTS 5,776,124 A * 7/1998 Wald .......................... 604/403
6,070,623 A * 6/2000 Aneas ......................... 141/27
6,071,270 A * 6/2000 Fowles et al. ......... 137/614.04
6,139,534 A * 10/2000 Niedospial et al. ......... 604/403

FOREIGN PATENT DOCUMENTS

JP 07213585 8/1995
JP 7213585 * 8/1995

* cited by examiner

*Primary Examiner*—Gene Mancene
*Assistant Examiner*—John Fristoe
(74) *Attorney, Agent, or Firm*—Birch, Stewart, Kolasch & Birch, LLP

(57) ABSTRACT

An adapter for mixing and injection of preparations comprises a cylindrical vial-fitting portion (1), a puncture needle (2) and a tubular tip-fitting portion (3). The vial-fitting portion (1) includes a top wall (11) and a skirt (12). The puncture needle (2) is passed through the top wall (11) and is integrated therewith. The tip-fitting portion (3) is arranged coaxially to the puncture needle (2) on the opposite side thereof to the top wall (11). The puncture needle 2 has a cutting edge 21 on the side of the skirt (12) and is provided at a proximal end thereof with a connecting portion (22) for engagement with the tip-fitting (23), which communicates with a lumen (32) of the tip-fitting portion (3) and is open to the cutting edge (21). A filter (4) is arranged in the liquid passage (231) of the connecting portion (22).

6 Claims, 5 Drawing Sheets

ADAPTER FOR MIXING AND INJECTION OF PREPARATIONS

BACKGROUND OF THE INVENTION

1. Field of the Invention

The present invention relates to an adapter for mixing and injection of preparations. More particularly, the present invention relates to an adapter for transferring a drug solution or solvent from a syringe to a vial including a dried medicine such as a powdered preparation or a solid preparation charged therein to mix them to prepare a dose of a mixed medical solution and for transferring the resultant medical solution in the vial to the syringe.

2. Description of Background Art

Freeze-dried medicines such as powdered preparations or solid preparations are generally stored in vials. In the prior art, such preparations are mixed with a solvent or drug solution, for example, by connecting a vial to a solvent vessel with a double-ended needle to form liquid communication between them, transferring the solvent from the solvent vessel to the vial to dissolve the dried medicine in the solvent, and collecting a certain amount of the resultant drug solution by a syringe through a needle attached thereto.

However, the above method takes a long time to fill the syringe with the resultant drug solution by suction because of a minor diameter of the needle to be used. Further, in order to avoid risk of an accident due to use of an edged metal needle, it is difficult to operate.

In order to solve such disadvantages, it has been proposed in Japanese patent unexamined publication JP-A 7-213585 to use an adapter for liquid transfer and injection, which is connectable to both a vial and a syringe and makes it possible to transfer the liquid without use of any syringe needle. This adapter comprises a cylindrical hub coaxially provided at one end thereof with a hollow puncture needle and at the opposite end with a tubular tip-fitting portion. At the peripheral part of the hub, there are provided a vial-fitting portion and a syringe-connecting portion, which are respectively coaxial to the puncture needle and the tip-fitting portion. The puncture needle is provided with a medicine channel communicated with the tip-fitting portion, and a gas channel being open to a vent hole with a filter for separation of microorganisms provided in the vial-fitting portion.

However, the above adapter for liquid transfer and injection has a danger of contamination in the medical solution with foreign substances due to coring which may occur by puncture of a rubber stopper with the puncture needle.

SUMMARY AND OBJECTS OF THE INVENTION

In view of the above circumstances, the present invention has been made to provide an adapter for mixing and injection of preparations, which makes it possible to remove foreign substances get into a medical solution in case of operation to dissolve a dose of a solid preparation in a solvent by use of the adapter.

According to the present invention, the above object is achieved by providing an adapter with a filter, in particular, by providing a connecting portion for attachment to the tip-fitting portion at a proximal end of a puncture needle and arranging a filter in the connecting portion. This makes it possible to provide a filter in the adapter with ease and certainty.

In other words, the present invention provides an adapter for mixing and injection of preparations comprising:

a vial-fitting portion having a top wall and a skirt portion;

a puncture needle passed through the top wall 11 of the vial-fitting portion 1 and integrated therewith, said puncture needle having a cutting edge on the side of said skirt; and a tubular tip-fitting portion located coaxially to the puncture needle on the opposite side thereof to the top wall, wherein said puncture needle has at a proximal end thereof a connecting portion for connection with the tip-fitting portion and a liquid passage which communicates with a lumen of the tip-fitting portion and is open to the cutting edge of the puncture needle, said connecting portion being provided at a liquid passage thereof with a filter.

In order to facilitate the transfer of liquid from a syringe to a vial or vice verse, the puncture needle may be provided with a gas passage running through the puncture needle and being open to the cutting edge while the connecting portion of the puncture needle may be provided with a vent hole having a filter for separation of microorganisms and being communicated with the gas passage. In this case, it is preferred to provide a check valve, which allows the gas to flow only in the direction of the gas passage, adjacent to the filter in the vent hole on the inside of the filter, so as to prevent the medical solution from flowing into the vent hole through the gas passage when the vial is reversed.

Further, in order to facilitate the attachment of the vial to the adapter, the vial-fitting portion may be provided in its skirt with one or more vertical slit.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
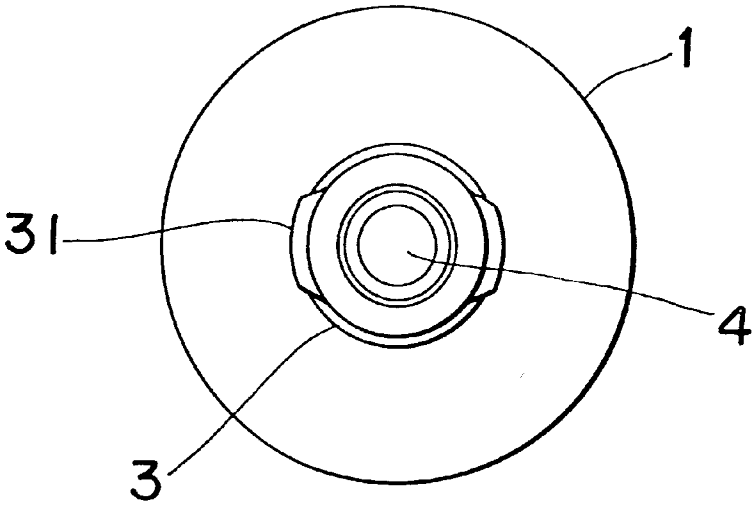
FIG. 1 is a plane view of an adapter for mixing and injection of preparations illustrating one embodiment of the present invention.
Figure 2:
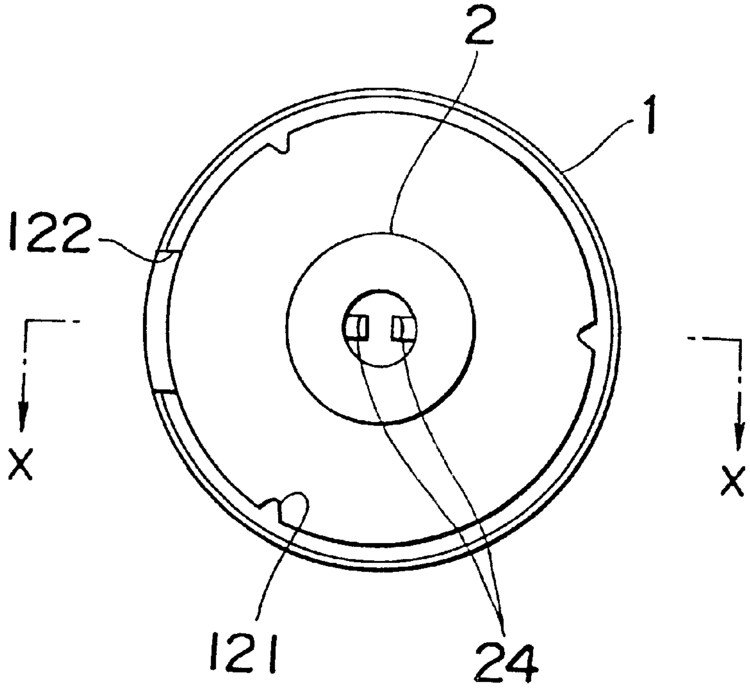
FIG. 2 is a bottom view of the adapter shown in FIG. 1.
Figure 3:
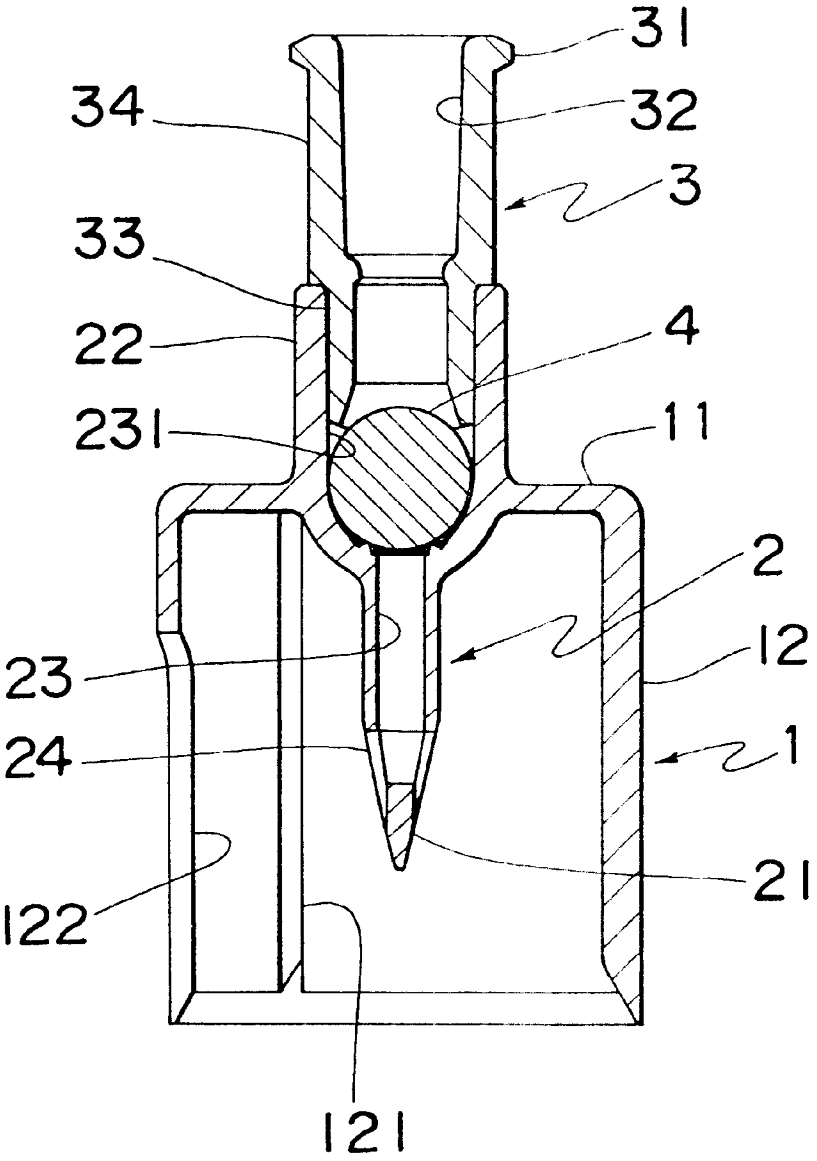
FIG. 3 is a section view of the adapter taken along a line X—X in FIG. 2.

Referring now to FIGS. 1 to 3, there is illustrated one embodiment of an adapter for mixing and injection of preparations according to the present invention, which comprises a cylindrical vial-fitting portion 1, a puncture needle 2, and a tubular tip-fitting portion 3. The vial-fitting portion 1 includes a top wall 11 and a skirt 12. The puncture needle 2 is passed through the top wall 11 and is integrated therewith. On the other hand, the tip-fitting portion 3 is arranged coaxially to the puncture needle 2 on the opposite side thereof to the top wall 11 and connected to the proximal end of the puncture needle 2.

The puncture needle 2 has a cutting edge 21 on the side of the skirt 12 and is provided at a proximal end thereof with a connecting portion 22 for engagement with the tip-fitting portion 3. The puncture needle 2 has a fluid passage 23, which communicates with a lumen 32 of the tip-fitting portion 3 and is open to the cutting edge 21. A filter 4 is arranged in the liquid passage 231 of the connecting portion 22.

The vial-fitting portion 1 is a cylindrical member made of a flexible material such as polypropylene, polyethylene, ABS resin, polycarbonate resin, polystyrene resin or the like and having the top wall 11 and skirt.12. The skirt 12 is provided on an inner wall thereof with three or five longitudinal ribs 121 to enhance the engagement force with the vial (not illustrated in the drawings). Further, the skirt 12 may be provided with one or more longitudinal slit 122 to facilitate insertion of the vial.

The puncture needle 2 is passed through the top wall 11 of the vial-fitting portion 1 and integrated therewith. The puncture needle 2 has a cutting edge 21 on the side of the skirt 12 of the vial-fitting portion 1 and has a connecting portion 22 for attachment of the tip-fitting portion 3 at the proximal end thereof. The needle has a liquid passage 23, which communicates with a lumen 32 of the tip-fitting portion 3 and is open to the cutting edge 21 through side holes 24. The liquid passage 23 is increased in diameter at the connecting portion 22 to form a large-sized liquid passage 231. Arranged in the large-sized liquid passage 231 is a filter 4 for removal of foreign substances due to coring, which may occur by puncture of a rubber stopper in a mouth of the vial with the puncture needle 2.

The filter 4 may take any shape and may be made of any material, provided that it can remove the foreign substances. It is preferred to use a layered material of wire netting, fibers or sintered compact of resin. The filter 4 may be formed into a spherical body as illustrated in FIG. 3. In this case, since the filter 4 has no orientation, it is easy to arrange the filter 4 in the connecting portion 22. Further, when fitting the separate tip-fitting portion 3 in the connecting portion 22, it is possible to fix the filter 4 in position by forcing the filter 4 toward a seating portion therewith.

The tip-fitting portion 3 may be formed as an integral part of the vial-fitting portion 1 and the puncture needle 2. Preferably, the tip-fitting portion 3 may be formed as a discrete member separated from the vial-fitting portion 1 and the puncture needle 2 as illustrated in FIG. 3. In this case, tip-fitting portion 3 is composed of a distal portion 33 to be fitted in the connecting portion 22 of the puncture needle 2, and a proximal portion 34 to be connected to a tip C of a syringe S illustrated in FIG. 7. The proximal portion 34 may be provided at a proximal end thereof with a double-start thread 31 as an engaging means, if necessary. In this case, it is possible to fix a syringe with a female engaging means (not illustrated in the drawings) on the tip C.

Figure 4:
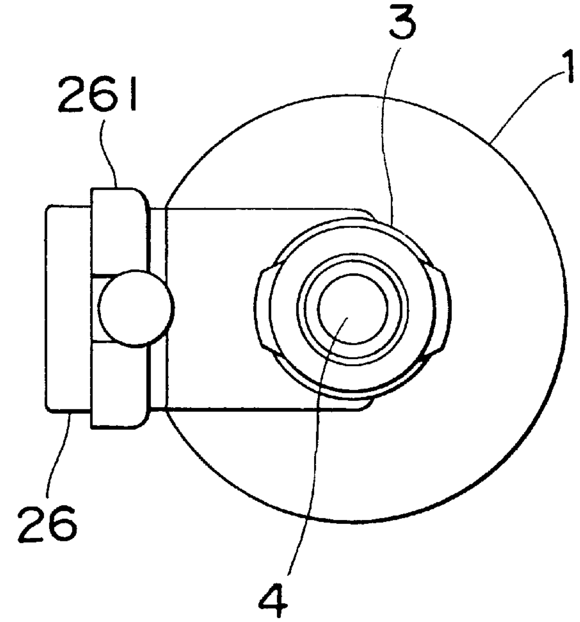
FIG. 4 is a plane view illustrating another embodiment of the adapter according to the present invention.
Figure 5:
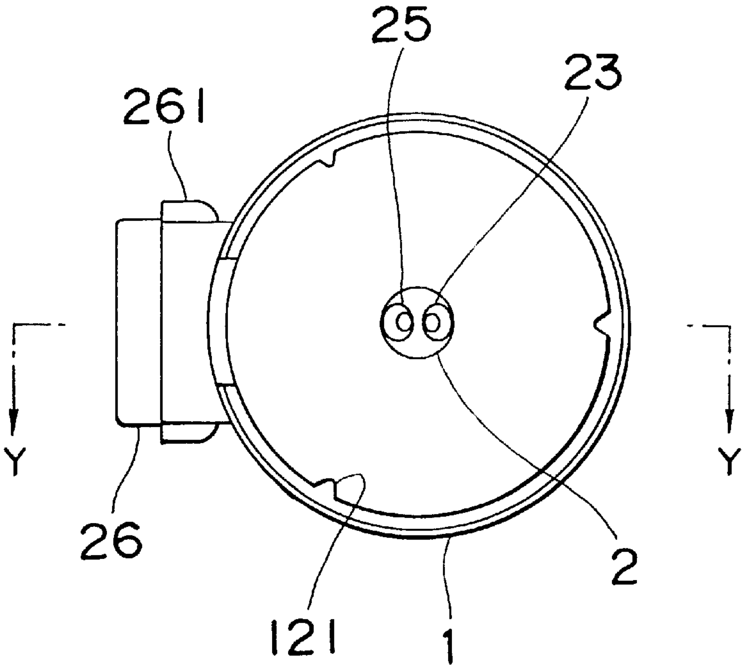
FIG. 5 is a bottom view of the adapter shown in FIG. 4.
Figure 6:
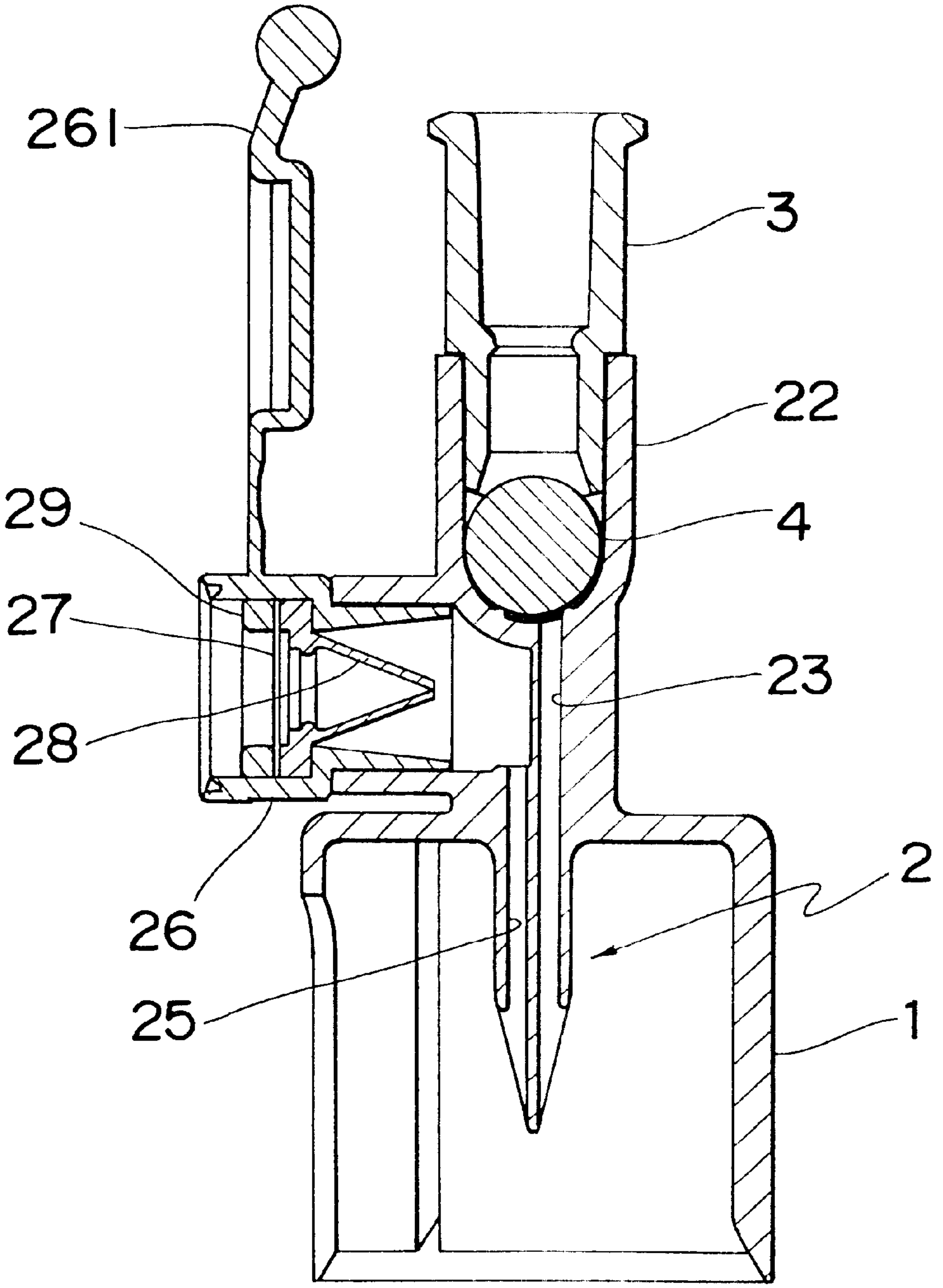
FIG. 6 is a section view of the adapter taken along a line Y—Y in FIG. 5.

As illustrated in FIGS. 4 to 6, the puncture needle 2 may be provided with a gas passage 25 being open to the cutting edge 25 and a vent hole 26 having a filter 27 for separation of microorganisms so that the gas passage 25 communicates with the vent hole 26. This makes it easy to perform the transfer of the medical solution. In this case, it is preferred to provide a check valve 28, which allows the gas to flow only in the direction of the gas passage 25, adjacent to the filter 27 in the vent hole 26 on the inside of the filter 27, so as to prevent the medical solution from flowing into the vent hole 26 through the gas passage 25 when the vial is reversed. The check valve 28 is fixed in position by a stopper ring 29. A reference numeral 261 is a cap for closing a vent hole 26. It is not necessary to provide the cap if the check valve 28 is provided in the vent hole 26.

Figure 7:
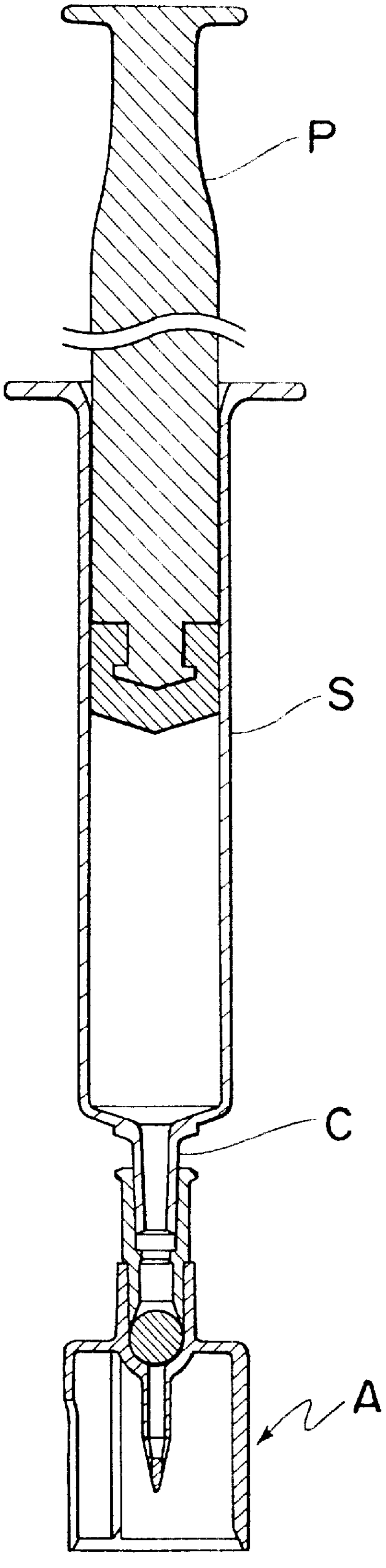
FIG. 7 is a side view illustrating how to use the adapter of FIG. 1.

Use of the adapter for mixing and injection of preparations of the present invention will be explained below with reference to FIG. 7. The adapter for mixing and injection of preparations of the present invention is used under the condition where the tip C of the syringe S is fitted in the tip-fitting portion 3. Under such a condition, a vial (not illustrated) is fitted in the vial-fitting portion 1, thereby piercing the rubber stopper of the vial with the puncture needle 2 to communicate the syringe S with the vial. After this, a plunger rod P is pushed to transfer a solvent in the syringe S to the vial. The medicine in the vial is dissolved in the transferred solvent by shaking the vial to prepare a medical solution. The prepared medical solution in the vial can be sucked in the syringe S by pulling back the plunger rod P.

As will be understood from the above description, the use of the adapter of the present invention makes it possible to remove any foreign substances which are mixed in the medical solution during operation to dissolve the medicine in the solvent with the adapter for mixing and injection of preparations. Further, the adapter is simple in construction, thus making it possible to manufacture adapters for mixing and injection of preparations at a low price.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An adapter for mixing and injection of preparations comprising:

a vial-fitting portion having a top wall and a skirt portion;

a puncture needle passed through the top wall of the vial-fitting portion and integrated therewith, said puncture needle having a cutting edge on the side of said skirt; and a tubular tip-fitting portion located coaxially to the puncture needle on the opposite side thereof to the top wall, wherein said puncture needle has at a proximal end thereof a connecting portion for connection with the tip-fitting portion and a liquid passage which communicates with a lumen of the tip-fitting portion and is open to the cutting edge of the puncture needle, said connecting portion being provided at a liquid passage thereof with a first filter, said first filter being formed into a substantially spherical body so that orientation of said first filter is not necessary when arranging said first filter in said connecting portion.

2. The adapter for mixing and injection of preparations according to claim 1, wherein said puncture needle is provided with a gas passage which is open to the cutting edge, and wherein said connecting portion is provided with a vent hole with a second filter for separation of microorganisms, said gas passage being communicated with the vent hole.

3. The adapter for mixing and injection of preparations according to claim 2, wherein said vent hole is provided with a check valve close to and inside of the second filter, said check valve allowing the gas to flow only in the direction of the gas passage.

4. The adapter for mixing and injection of preparations according to claim 1, wherein said vial-fitting portion is provided at the skirt thereof with a longitudinal slit extending from a distal end of the skirt toward said top wall for facilitating insertion of a vial.

5. The adapter for mixing and injection of preparations according to claim 1, wherein the tip-fitting portion is formed as a discrete member separated from the vial-fitting portion and puncture needle, and wherein the tip-fitting portion is fitted in the connecting portion of the puncture needle to hold the first filter.

6. The adapter for mixing and injection of preparations according to claim 1, wherein the tip-fitting portion is provided at a proximal end thereof with a double-start thread and engaged with female engaging means provided on the tip of the syringe.

* * * * *